United States Patent

Kreuzer

[11] Patent Number: 4,591,122
[45] Date of Patent: May 27, 1986

[54] SUPPORT STRUCTURE WITH A SUPPORT ARM PIVOTAL FOR HEIGHT ADJUSTMENT

[76] Inventor: Friedhelm Kreuzer, Zwiedineckstrasse 16, 8000 Munich 50, Fed. Rep. of Germany

[21] Appl. No.: 617,466

[22] Filed: Jun. 5, 1984

[30] Foreign Application Priority Data

Jun. 6, 1983 [DE] Fed. Rep. of Germany ....... 3320437
May 7, 1984 [DE] Fed. Rep. of Germany ....... 3416823

[51] Int. Cl.⁴ ................................................ E04G 3/00
[52] U.S. Cl. ................................ 248/280.1; 248/281.1
[58] Field of Search ............... 248/123.1, 280.1, 292.1, 248/324, 585, 281.1, 642, 574; 403/112

[56] References Cited

U.S. PATENT DOCUMENTS

| | | | |
|---|---|---|---|
| 911,935 | 2/1909 | Baumwart | 248/123.1 X |
| 2,766,007 | 10/1956 | Krilanovich | 248/281.1 X |
| 3,421,723 | 1/1969 | Holt | 248/652 |
| 4,082,244 | 4/1978 | Groff | 248/280.1 |
| 4,158,490 | 6/1979 | Gottschalk et al. | 248/281.1 X |
| 4,160,536 | 7/1979 | Krogsrud | 248/280.1 |
| 4,166,602 | 9/1979 | Nilsen et al. | 248/123.1 X |
| 4,208,028 | 6/1980 | Brown et al. | 248/123.1 X |

Primary Examiner—Ramon S. Britts
Assistant Examiner—David M. Purol
Attorney, Agent, or Firm—Craig & Burns

[57] ABSTRACT

A support structure with a support arm pivotal for purposes of height adjustment which is balanced by means of a spring and includes at its free end a mounting structure for apparatus, for example, medicinal apparatus or data processing apparatus. The support arm of the support structure includes a support frame and at least two connecting rods which, for purposes of forming two parallelogram guidances, are connected at one end thereof with a guide element and at the other end thereof with a connecting member. The connecting members as also the guide element are rotatably mounted on the support frame. For balancing the weight, at least one compression spring is installed between the support frame and the guide element. In a preferred embodiment, gas pressure springs are used as compression springs.

25 Claims, 1 Drawing Figure

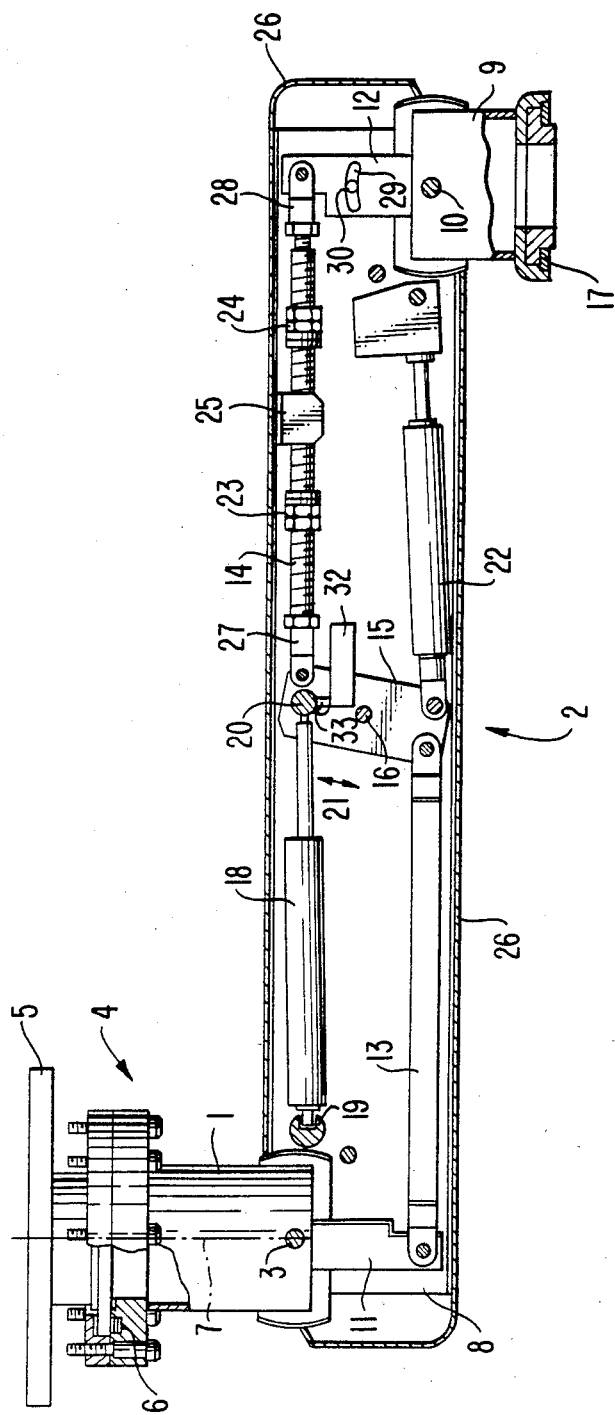

SUPPORT STRUCTURE WITH A SUPPORT ARM PIVOTAL FOR HEIGHT ADJUSTMENT

The present invention relates to a support structure or stand with a support arm or cantilever beam pivotal for height adjustment, which is weight-balanced by a spring and includes at its free end a mounting means for apparatus and the like.

Such support structures are used, for example, as ceiling supports or floor supports for holding medicinal apparatus of all types or data processing apparatus.

In a prior art support structure of the aforementioned type, two self-supporting half-shells, which are connected with each other in the manner of a parallelogram guidance, form the support arm, respectively, cantilever beam. A tension spring stressed between the half-shells assures for a compensation and balance of the weight of the apparatus secured at the support arm so that the apparatus can be positioned at will within the adjusting range without the use of any large force.

Since the weights carried by such support structures may amount up to 50 kp or more, the use of a very strong tension spring is necessary in the prior art support structures. The risk is correspondingly great that the tension spring will break by reason of fatigue phenomena.

Furthermore, it is frequently required with support structures of the aforementioned type that feed lines, for example, gas lines, electric lines, etc. are to be extended through the support structure to the apparatus secured thereon. By reason of the self-supporting type of construction, the accommodation of lines in the support arm of the prior art support structure is possible only with a relatively large expenditure of work.

Accordingly, it is the principal object of the present invention to so further develop and construct a support structure of the aforementioned type that the use of a tension spring can be dispensed with.

The underlying problems are solved according to the present invention in that the support arm includes a support frame and at least two connecting rods which, for purposes of forming two parallelogram guidances, are pivotally connected with one end thereof at a guide element that is rotatably supported on the support frame, and with the other end thereof to a connecting member each, which are also rotatably mounted on the support frame, and in that at least one compression spring is inserted between the support frame and the guide element. By the use of two parallelogram guidances connected with each other by way of a guide element, it becomes possible to balance the weight by means of a compression spring, with which the danger of a breakage, etc. is considerably smaller.

The support structure according to the present invention therebeyond offers the following advantages:

The construction with a guide element permits a construction of the support arm which is identical on the load side and on the side of the pivotal connection, i.e., on the side of the support column.

Additionally, the use of a support frame permits the easy accommodation of feed lines.

Furthermore, it is possible in case of large counter-forces to be produced to insert several compression springs in parallel.

Owing to the adjustability of the point of pivotal connection of the compression spring, respectively, compression springs in accordance with the present invention, the produced counter-force can be matched to the weight of the retained apparatus. It is thereby of particular advantage if, in case of several parallely connected compression springs, the adaptability of the counterforce by adjustment of the point of pivotal connection is larger than the counter-force produced by a compression spring.

If, according to another feature of the present invention, the compression spring or springs are inserted into blind-end bores provided in shafts which are mounted at the support frame, respectively, at the guide element, an easy insertion and easy removal of compression springs is realized thereby. By reason of the concept in accordance with the present invention, a removal and an insertion of the compression springs in the unstressed condition is possible. For that purpose, the support arm is merely pivoted beyond its normal pivot range and the compression spring is removed, respectively, installed.

The use of gas compression springs not only further reduces the risk that the compression spring experiences a sudden failure and therewith the retained load is dropped, but also leads to a greater insensitivity with respect to fluctuations of the weight of the retained load by reason of the larger friction in the gas compression spring.

In particular with heavy loads or also in operating rooms, the use of a motor-driven adjusting member is very advantageous since it permits, for example, a height adjustment without touching the support arm.

According to still another feature of the present invention, the fixing of the support arm may take place in different ways, for example, by the use of a releasable stop spring or by the use of a pin at the support frame which engages in a groove concentric to the axis of rotation of the apparatus mounting and provided in the connecting member on the load side, whereby the pin may be constructed as clamping screw.

If, according to still another feature of the present invention, one of the connecting rods is a threaded rod, over which are screwed nuts which together with an element secured at the support frame form an abutment for the limitation of the height adjustment of the support arm, not only a simple construction of the abutments for the height adjustment of the support structure is possible thereby but therebeyond also the support arm can be fixed by simple means.

The construction of the support structure according to the present invention with a support frame and a removable covering enables not only an easy insertion of the feed lines but therebeyond—differing from self-supporting half-shells—prevents the penetration of dirt.

These and further objects, features and advantages of the present invention will become more apparent from the following description when taken in connection with the accompanying drawing which shows, for purposes of illustration only, one embodiment in accordance with the present invention, and wherein:

The single figure is a somewhat schematic partial cross-sectional view through a support structure in accordance with the present invention.

The support structure according to the present invention includes a support column 1 and a support arm, respectively, cantilever beam generally designated by reference numeral 2 which is pivotal in a perpendicular plane—i.e., in the plane of the drawing—about a shaft 3.

In the illustrated embodiment, the support column 1 is connected by way of a flange generally designated by reference numeral 4 with an element 5 adapted to be connected with the room ceiling, i.e., the support structure is a ceiling support. Of course, the features according to the present invention are also applicable, for example, with a floor support, etc.

A slide bearing 6 is provided in the flange 4 so that the support column 1 together with the support arm 2 can be rotated about an axis 7.

The support arm, respectively, cantilever 2 includes a support frame 8 which is pivotally connected at the shaft 3. The support frame 8 is formed of two U-shaped profiles, not illustrated in detail, which butt with their legs and are welded together by means of a flat steel bar each. This reinforcement of the support frame offers the additional advantage of reducing the bearing pressure for the inserted shafts, respectively trunions.

At the end of the support arm 2 opposite the pivot shaft 3, a suspension arrangement 9 for apparatus mountings, etc. is pivotally connected at the support frame 8 pivotal about a shaft 10 extending parallel to the shaft 3.

Additionally, one connecting member 11, respectively, 12 is pivotally connected at the shafts 3 and 10, to the other end of which is pivotally connected one connecting rod 13, respectively, 14 each. The other end of the connecting rods 13 and 14 is pivotally connected at a guide element 15 which is rotatably secured at the support frame 8 about a shaft or trunion 16 also parallel to the shaft 3.

The connecting members 11 and 12, the connecting rods 13 and 14, as well as the guide element 15 form two parallelogram guidances, by means of which the abutment surface 17 of the suspension installation 9 for apparatus, etc. is held always horizontally independently of the position of the support arm 2.

For balancing the weight of the support arm 2 as well as of the apparatus secured thereon, a spring 18 is provided so that in case of height adjustment of the support arm 2, only the friction has to be still overcome. By reason of the construction in accordance with the present invention including parallelogram guidances having a guide element 15, this spring 18 is a compression spring and not a tension spring as in the prior art parallelogram guidances. Advantageously, a gas compression spring is used in accordance with the present invention as compression spring.

In the illustrated embodiment, the compression spring 18 is inserted with its ends in blind-end bores (not shown in detail) provided in shafts 19 and 20 which are pivotally connected to the support frame 8 and the guide element 15, respectively. For adjusting the counter-force produced by the compression spring 18, the shaft 20 is displaceable at the guide element 15 in the direction of an arrow 21.

For fixing the support arm 2 in a predetermined position, a stop spring 22 is provided which, on the one hand, is pivotally connected at the guide element 15 and, on the other, at the support frame 8. The stop spring 22 is, for example, a gas spring whose length is adjustable only after the opening of a valve. The valve can be opened, for example, by way of a Bowden cable (not shown) or by means of compressed air.

In the illustrated embodiment, the connecting rod 14 is additionally a threaded rod, on which are screwed counter or check nuts 23, respectively, 24. The nuts 23 and 24 form, together with an element 25 secured at the support frame 8, adjustable stops, by means of which the height-adjusting range of the support arm 2 can be limited. Possibly the height-adjusting range is thereby adapted to be limited to the value 0, i.e., the support arm is rigidly secured in a predetermined position.

The connecting rod 14 additionally includes at its two ends threads with differing pitches, for example, an M10-thread with a pitch of 1.5 mm. is provided at the end on the load side and an M14-thread with a pitch of 2 mm. is provided at the end on the side of the guide element 15, by means of which the connecting rod 14 is screwed together with elements 27 and 28 which in turn are pivotally connected at the guide element 15, respectively, at the connecting member 12. As a result thereof, it is possible by rotation of the connecting rod 14 to adjust the inclination of the connecting member 12 in relation to the guide element 15. For example, manufacturing tolerances can be compensated thereby which otherwise would lead to the fact that the abutment surface 17 for apparatus, etc. is not aligned horizontally.

Furthermore, the support arm 2 includes a detachable covering 26 consisting of two half-shells so that lines, etc. can be easily installed in the support arm.

The support structure according to the present invention offers a number of advantages.

By the use of a guide element 15 in the parallelogram guidance, not only the use of a compression spring in lieu of a tension spring is possible but also a symmetric construction of the support arm becomes possible which is constructed identically on the side of the load and on the side of the column. As a result thereof, the manufacturing costs are considerably reduced.

Therebeyond, the removal and installation of the compression springs is possible in the unstressed condition. The support arm is simply pivoted beyond its normal pivot range and the unstressed compression spring is removed.

This makes it possible to match the counter-force to the weight of the retained apparatus by installation of several compression springs next to one another between the shafts 19 and 20, respectively, by removal of compression springs. The adjustment possibility of the counter-force by displacement of the shaft 20 in the direction of the arrow 21 is thereby advantageously made larger than the counter-force produced by a compression spring.

While I have shown and described only one embodiment in accordance with the present invention, it is understood that the same is not limited thereto but is susceptible of numerous changes and modifications as known to those skilled in the art. For example, it is possible to utilize two connecting members 11 and 12 and two connecting rods 13 and 14 as well as two guide elements 15 each, between which extends the shaft 20, into which the compression springs are inserted. Additionally, two parallel rods with transverse reinforcements may be used as support frame 8, which are formed by the different trunions, respectively, shafts. Furthermore, the stop spring 22 can be replaced by a pin 29 at the support frame 8, which engages in a groove 30 concentric to the shaft 10 and provided in the connecting member 12. A braking action results from the friction between the pin 29 and the groove 30. Furthermore, if one constructs the pin as threaded element, the support arm 2 can be fixed in any desired position. Moreover, the suspension arrangement 9 as also the support column 1 may be constructed rotatable about a vertical axis.

Furthermore, in addition or in lieu of the compression springs 18, one or several motor-driven adjusting members may be used, such as hydraulic cylinders, etc.

which serve for the adjustment and/or weight-balancing of the support arm. Consequently, I do not wish to be limited to the details shown and described herein, but intend to cover all such changes and modifications as are encompassed by the scope of the appended claims.

I claim:

1. A support structure comprising a support arm means pivotal for purposes of height adjustment, means including spring means for balancing the weight of the support arm means, mounting means at the free end of the support arm means for retaining thereat apparatus, the support arm means including a support frame means and at least two connecting rods which, are pivotally connected at one end thereof with a guide means and at the other end thereof with separate connecting members forming two parallelogram guidances, said guide means and said connecting members being rotatably supported on said support frame means, and at least one compression spring means installed between the support frame means and the guide means.

2. A support structure according to claim 1, further comprising means for adjusting the point of pivotal connection of the compression spring means at the guide means to adjust the counter-force produced by the compression spring means.

3. A support structure according to claim 2, wherein said point of pivotal connection is adjustable steplessly.

4. A support structure according to claim 2, wherein said point of pivotal connection is adjustable in steps.

5. A support structure according to claim 3, wherein said compression spring means is adapted to be inserted into dead-end bores provided in shafts which are mounted at said support frame means and guide means.

6. A support structure according to claim 5, wherein said compression spring means are gas pressure springs.

7. A support structure according to claim 6, further comprising a motor-driven adjusting member for the adjustment and balancing of the weight.

8. A support structure according to claim 7, wherein said motor-driven adjusting member is used in lieu of the compression spring means.

9. A support structure according to claim 7, further comprising means including a releasable stop spring for fixing the support arm means.

10. A support structure according to claim 7, further comprising means including a pin for fixing the support arm means at the support frame means, said pin engaging in a groove concentric to the axis of rotation of the mounting means, said groove being provided in one of the connecting member.

11. A support structure according to claim 10, wherein said pin is constructed as clamping screw.

12. A support structure according to claim 6, wherein one of said connecting rods is a threaded rod, onto which are screwed nuts which together with an element secured at the support frame means form an abutment for limiting the height adjustment of the support arm means.

13. A support structure according to claim 12, wherein the support structure is pivotal about a vertical axis.

14. A support structure according to claim 6, wherein said support frame means is formed by two welded-together U-shaped profiles within which are arranged the parallelogram guidances.

15. A support structure according to claim 6, wherein two parallel strut-like members form the support frame means.

16. A support structure according to claim 15, wherein a removable covering means is provided on the support frame means.

17. A support structure according to claim 14, wherein a removable covering means is provided on the support frame means.

18. A support structure according to claim 1, wherein each compression spring means is adapted to be inserted into dead-end bores provided in shafts which are mounted at said support frame means and guide means.

19. A support structure according to claim 1, wherein said compression spring means are gas pressure springs.

20. A support structure according to claim 1, further comprising means including a releasable stop spring for fixing the support arm means.

21. A support structure according to claim 1, further comprising means including a pin for fixing the support arm means at the support frame means, said pin engaging in a groove concentric to the axis of rotation of the mounting means, said groove being provided in the connecting member on the side of the load.

22. A support structure according to claim 1, wherein one of said connecting rods is a threaded rod, onto which are screwed nuts which together with an element secured at the support frame means form an abutment for limiting the height adjustment of the support arm means.

23. A support structure according to claim 1, wherein said support frame means is formed by two welded-together U-shaped profiles within which are arranged the parallelogram guidances.

24. A support structure according to claim 1, wherein two parallel strut-like members form the support frame means.

25. A support structure according to claim 1, further comprising a motor-driven adjusting member for the adjustment and balancing of the weight.

* * * * *